US011643316B2

(12) United States Patent
Soellner et al.

(10) Patent No.: US 11,643,316 B2
(45) Date of Patent: May 9, 2023

(54) DISTRIBUTION MACHINE FOR DISTRIBUTING FLOWABLE MEDIA

(71) Applicant: KRONES AG, Neutraubling (DE)

(72) Inventors: Juergen Soellner, Beratzhausen (DE); Waldemar Suppes, Neutraubling (DE); Florian Geltinger, Donaustauf (DE); Thomas Hoellriegl, Teublitz (DE); Andreas Brunner, Aufhausen (DE)

(73) Assignee: KRONES AG, Neutraubling (DE)

( * ) Notice: Subject to any disclaimer, the term of this patent is extended or adjusted under 35 U.S.C. 154(b) by 1022 days.

(21) Appl. No.: 16/461,895

(22) PCT Filed: Nov. 22, 2017

(86) PCT No.: PCT/EP2017/080047
§ 371 (c)(1),
(2) Date: May 17, 2019

(87) PCT Pub. No.: WO2018/095970
PCT Pub. Date: May 31, 2018

(65) Prior Publication Data
US 2019/0330039 A1 Oct. 31, 2019

(30) Foreign Application Priority Data
Nov. 22, 2016 (DE) ...................... 10 2016 122 542.8

(51) Int. Cl.
B67C 3/26 (2006.01)
A61L 2/20 (2006.01)
B67C 3/22 (2006.01)

(52) U.S. Cl.
CPC ............ *B67C 3/2642* (2013.01); *A61L 2/208* (2013.01); *A61L 2202/23* (2013.01); *B67C 2003/228* (2013.01)

(58) Field of Classification Search
CPC . B67C 3/2642; B67C 2003/228; A61L 2/208; A61L 2202/23
(Continued)

(56) References Cited

U.S. PATENT DOCUMENTS 5,653,091 A * 8/1997 Stark ................. B65B 55/04
53/484
6,644,363 B2 * 11/2003 Sogliani ................. B67C 3/202
141/94
(Continued)

FOREIGN PATENT DOCUMENTS

DE 102006053193 5/2008
DE 102007041685 3/2009
(Continued)

OTHER PUBLICATIONS

International Search Report dated Apr. 11, 2018 issued in corresponding International Application No. PCT/EP2017/080047.
(Continued)

*Primary Examiner* — Andrew M Tecco
(74) *Attorney, Agent, or Firm* — Onello & Mello, LLP

(57) ABSTRACT

Machine (1) for distributing flowable media to containers with a housing (2), with a transport device (12) for transporting the containers (10) which is arranged at least partially inside the housing (2), wherein this transport device has a rotatable carrier (14) with a distributor device (4) which is arranged inside this housing (2) an accommodates at least one inlet (42) for the flowable medium and a plurality of outlets (44) to which the flowable medium can be distributed, and with a supply conduit (6) which is suitable and intended for supplying the flowable medium to the inlet (42). According to the invention the distributor device (4) is non-rotatably connected to the carrier (14).

11 Claims, 4 Drawing Sheets

(58) Field of Classification Search
USPC .................................. 53/561, 425; 141/92
See application file for complete search history.

(56) References Cited

U.S. PATENT DOCUMENTS

| | | | |
|---|---|---|---|
| 7,699,080 B2* | 4/2010 | Burgmeier | B67C 3/22 |
| | | | 422/302 |
| 7,900,422 B2 | 3/2011 | Fischer | |
| 10,377,519 B2* | 8/2019 | Brandenburger | B67C 7/00 |
| 2009/0056828 A1* | 3/2009 | Burgmeier | B67C 3/22 |
| | | | 141/242 |
| 2010/0199604 A1* | 8/2010 | Fischer | B67C 7/0073 |
| | | | 53/425 |
| 2012/0018030 A1* | 1/2012 | Laumer | B67C 3/001 |
| | | | 141/89 |
| 2016/0244195 A1* | 8/2016 | Brandenburger | B65B 43/46 |

FOREIGN PATENT DOCUMENTS

| | | | | |
|---|---|---|---|---|
| DE | 102011056440 A1 * | 6/2013 | | A61L 2/20 |
| DE | 102012109884 | 4/2014 | | |
| EP | 2604295 | 6/2013 | | |
| EP | 2722304 | 4/2014 | | |

OTHER PUBLICATIONS

German Search Report dated Apr. 12, 2017 issued in corresponding German Application No. 102016122542.8.
European Office Action dated Mar. 30, 2022 issued in corresponding European Application No. 17811867.5.

* cited by examiner

DISTRIBUTION MACHINE FOR DISTRIBUTING FLOWABLE MEDIA

The present invention relates to a machine and a method for distributing flowable media. Such machines and methods have been known for a long time from the prior art. Thus for example rotary distributors are known, which distribute liquid from a tank to a plurality of filling conduits. In the field of sterilisation technology such distributor devices are known which distribute a sterilising agent and in particular a liquid or gaseous sterilising agent to a plurality of outlets such as for instance nozzles.

In this case such distributor devices usually have rotary distributors, since in the prior art the containers to be processed are usually conveyed by means of a rotatable carrier, that is to say along a circular path. So it is known, for example, that a sterilising medium, such as for example $H_2O_2$ is fed via a stationary top to a processing chamber and is conveyed via a distributor chamber, which is suspended rotatably by hybrid bearings, to the individual processing stations. These procedure has become technically well-established, but is relatively complex and expensive. In particular in these solutions hybrid bearings are also used which themselves already have very high prices.

In addition, such structures also have a elaborate connection structure for embedding the bearings. In addition such bearings are also vulnerable in the event of incorrect mounting. Corresponding seals currently also do not have to seal completely, since for example a sterilising medium in any case flows into the respective processing chamber.

Therefore the object of the present invention is to provide a machine which dispenses with the use of the expensive bearings described above and which can be produced more favourably in this way. This object is achieved according to the invention by the subject matter of the independent claims. Advantageous embodiments and modifications are the subject matter of the subordinate claims.

A machine according to the invention for distributing flowable media to containers has a housing and a transport device for transporting the containers which is arranged at least partially inside the housing. In this case the transport device has a rotatable carrier. In addition a distributor device is provided which is arranged inside this housing and has at least one inlet for the flowable medium this transport device and a plurality of outlets to which the flowable medium can be distributed. Advantageously in this case this inlet can be fluidically connected to the outputs. Furthermore, the machine has a feed conduit which is suitable and intended for feeding the flowable medium to the inlet.

According to the invention the distributor device is non-rotatably connected to the carrier.

Therefore in contrast to the prior art it is proposed that the distributor device is not supported by means of the above-mentioned expensive bearings, but is non-rotatably or mechanically connected to the carrier and thus is supported thereby. Preferably the distributor device is mechanically firmly connected to the carrier. In this case this carrier can be configured as a disc-shaped carrier. This carrier is preferably driven by means of a central shaft. The containers are in particular parisons, in particular plastic parisons. In addition, however, other containers could also be processed, such as for instance bottles and the like. Generally, however, the invention can also be applied to other objects or piece goods which are to be processed.

In a further advantageous embodiment the above-mentioned transport device is a component of a processing device, in particular a device for sterilising preforms. The flowable medium is in particular (preferably gaseous) $H_2O_2$.

In a further preferred embodiment at least the machine in its entirety is arranged in a clean room. In addition to the said machine, further devices such as in particular, but not exclusively, transport starwheels can be arranged inside the clean room. This clean room is preferably demarcated by at least one wall relative to an (unsterile) environment.

The carrier is preferably a transport wheel, on which holding elements for holding containers are particularly preferably arranged. These holding elements can be for example gripping clips which can grip the containers, for example gripping clips which grip the containers in the region of the mouths thereof.

In an advantageous embodiment the flowable medium is gaseous or liquid. The flowable medium is particularly preferably hydrogen peroxide ($H_2O_2$) or peracetic acid. However, it would also be possible for the flowable medium to be a liquid, for example a liquid to be introduced into the containers.

In a further advantageous embodiment the distributor device is arranged on the carrier by means of mechanical fastening elements. These fastening elements can be for example fastening rods which support the distributor device.

In a further advantageous embodiment the housing forms a clean room, inside which sterile conditions (relative to an environment) can be produced. In this case this clean room can have walls which are movable relative to one another and which are particularly preferably sealed relative to one another. In a preferred embodiment the above-mentioned rotatable carrier also forms a wall delimiting the clean room.

In a further advantageous embodiment the feed conduit is arranged at least partially non-rotatably and the distributor device is rotatable relative to the feed conduit. The distributor device is preferably rotatable relative to a stationary axis of rotation. This axis of rotation is preferably a vertically extending axis of rotation. The axis of rotation about which the distributor device is rotatable is preferably parallel to the axis of rotation about which the carrier is rotatable, and particularly preferably these two axes of rotation coincide.

It is therefore proposed that the distributor chamber or distributor device is firmly connected to the rotating processing wheel. In this way it is possible to dispense with a bearing. A connection between a stationary top and a rotating distributor chamber preferably takes place, as described in greater detail below, by means of a sealing device for example to a bellows with a shaft sealing ring.

In a further advantageous embodiment the feed device extends through a cover section of the machine and/or a wall, in particular a top wall, delimiting the clean room. In this case this feed conduit is preferably stationary relative to the top wall. Particularly preferably the sealing device is located at least partially and preferred completely inside the said clean room. The machine preferably has pressure application means in order to generate an overpressure in the clean room relative to an ambient pressure.

Therefore, in a further advantageous embodiment a sealing device is arranged between the feed conduit and the distributor device. In this case this sealing device can preferably also be suitable and intended for guiding the flowable medium from the feed conduit to the inlet.

In a further advantageous embodiment the sealing device also serves in order to prevent the medium to be transported from escaping into the clean room.

In a further advantageous embodiment the inlet has an inlet conduit which is arranged non-rotatably on the distributor device and which can be fluidically connected to the feed conduit. In this case, particularly preferably, it is conceivable that this inlet conduit and the feed conduit have the same flow cross-section. If a bellows with a shaft sealing ring is used as a sealing device, it is conceivable that the bellows provides the compensation for tolerances and the shaft sealing ring provides the sealing function. In this case a co-rotation of the shaft sealing ring can be avoided by means of a torque support.

In a further advantageous embodiment the distributor device has a collecting compartment or a collecting chamber which serves for collecting the flowable medium fed by the feed device. In this case this collecting chamber can preferably be rotationally symmetrical with respect to a predetermined axis and in particular an axis of rotation about which this collecting chamber rotates during operation. This axis of rotation is preferably parallel to an axis of rotation of the carrier and particularly coincides therewith.

Furthermore, this collecting chamber preferably has a plurality of openings to which conduits can preferably be connected, which serve for further transport of the flowable medium to the individual containers.

However, it would also be conceivable that individual ones of these conduits do not convey the flowable medium to the containers, but to regions of the machine. In this way the flowable medium can also be used for cleaning the machine itself, for instance for carrying out a CIP (cleaning in place) cleaning. This is of great interest in particular in connection with a clean room, since in some circumstances it is possible to clean the clean room without having to open this clean room for this purpose.

Therefore, in a further advantageous embodiment the machine has a cleaning device for cleaning components of the machine itself. In this case this cleaning device is preferably configured in such a way that at least a part of a cleaning medium is also conveyed by means of the distributor device.

In a preferred embodiment, therefore, the stationary and the rotating part, and in particular the stationary feed conduit and the rotating inlet, are connected to one another by at least one flexible element. In this case in particular this flexibility is provided in the direction of this axis of rotation.

In this case it is possible that one end of this flexible sealing element is firmly fixed and the other end is rotatably mounted. This said end is preferably firmly fixed on a region of the feed conduit and the other end is rotatable relative to the inlet conduit. This feed conduit is preferably configured as a feed pipe.

In a further advantageous embodiment the sealing device is arranged between the inlet conduit and the feed conduit. Preferably, as mentioned above, the sealing device has a resilient element along the axis of rotation of the distributor device and/or preferably a bellows. In this case sealing can be provided for example by a sealing or a bellows.

In a further advantageous embodiment the bellows is made from a plastic. This plastic may particularly preferably be PTFE. In a further advantageous embodiment the flexible sealing element in the region of the shaft sealing ring is produced from a material different from that of the abovementioned bellows.

In a further advantageous embodiment the sealing region is produced from a plastic and particularly preferably substantially from PTFE (polytetrafluoroethylene). Particularly preferably this plastic is reinforced by a material which is selected from a group of materials which includes PEEK (polyether ether ketone), PI (polyimides) and PAI (polyamide-imides).

In a further advantageous embodiment the flexible sealing element is constructed in multiple parts and particularly preferably in two parts. In this case a part of this sealing element can be fastened for example to the feed conduit, whilst the second part slides and/or is rotatable relative to the inlet conduit.

In this case, furthermore possible, that the sealing region is held in its position by means of a support.

In a further advantageous embodiment the resilient element connects the feed conduit to the inlet of the distributor device and in particular to an inlet conduit of the inlet.

Furthermore, it is particularly preferably conceivable that a part of the said bellows is fixedly arranged on an element and preferably another end is arranged so that it slides or is rotatable relative to a further part.

In a further advantageous embodiment the sealing device has a bearing device for rotatable support of at least one element of the inlet or of the feed conduit. In particular the sealing device has a bearing device for rotatable support of the inlet conduit. This can be in particular a sliding bearing device.

In this way a particularly effective seal can be created.

In a further advantageous embodiment the bearing device is configured as a shaft sealing ring. A shaft sealing ring has become particularly well established, in order to achieve the rotatable support at the same time as maintaining a high sealing effect.

In a further advantageous embodiment the shaft sealing ring is made from a material different from that of the aforementioned bellows. In this case it is in particular conceivable that the flexible sealing element is in at least two parts. The sealing device can preferably have a circumferential sealing lip. The sealing lip preferably has a curved portion.

In a further advantageous embodiment the feed conduit and the distributor device are constructed without contact. This means that the connection between the stationary feed conduit and the rotating distributor chamber takes place without contact, so that the stationary feed conduit does not contact the rotating distributor chamber. There is preferably a gap of less than 15 mm, preferably less than 10 mm and particularly preferably less than 6 mm between the stationary component and the rotating component.

In a further advantageous embodiment sealing between the feed conduit and the distributor device takes place by a contactless labyrinth seal. Preferably, therefore, a sealing device is formed like a labyrinth between the feed conduit and the distributor device. Particularly preferably, the labyrinth seal is constructed in two parts, wherein a first part of the labyrinth seal is arranged on the stationary feed conduit and a second part of the labyrinth seal is arranged on the rotating distributor device. The respective stationary and rotating contours of the labyrinth or of the labyrinth seal are preferably substantially complementary. Preferably a leakage mass flow of less than 15% of the total mass flow can escape through the labyrinth seal.

In this case the labyrinth seal has the particular advantage that in this way, even by comparison with the abovementioned bellows solution, costs savings can again be made. Moreover, due to the lack of contact there is also no more friction or abrasion present, so that the wear can also be considerably reduced.

Furthermore, the present invention relates to a method for processing and in particular sterilising containers, wherein the containers are transported by means of a transport device and during this transport are acted upon by a flowable medium, and wherein the transport device has a rotatable support by means of which the containers are transported along a substantially circular path. In this case this carrier is located inside a housing (or delimits this housing), wherein the flowable medium is fed by means of a feed conduit to a distributor device likewise located inside this housing via an inlet and the distributor device distributes the flowable medium to a plurality of outlets.

According to the invention the distributor device is non-rotatably connected to the rotatable carrier.

It is therefore also proposed, in terms of the method, that the distributor device is not supported, as known in the prior art, by means of bearings, for example rolling bearings, but the support function is also provided here by the carrier.

The containers are preferably acted upon by the flowable medium, for example a sterilising agent, or a flowable medium as for instance a beverage is introduced into the containers.

In a further advantageous embodiment the flowable medium is conveyed from the distributor device via a plurality of conduits to the containers, for example in order to sterilise them.

Further advantages and embodiments are apparent from the appended drawings.

Figure 1A:
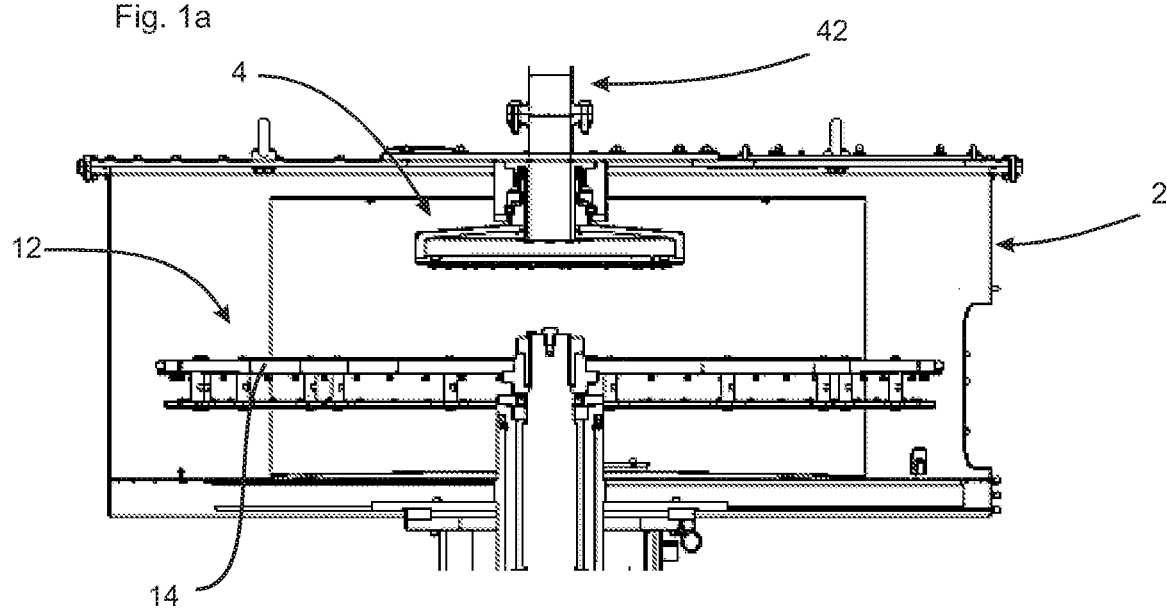
FIGS. 1a to 1c show three representations of a machine according to the prior art.

FIG. 1a shows a representation of a machine according to the prior art. In this case a feed conduit 42 is provided, by means of which a flowable medium is fed to a distributor device 4. The reference numeral 12 relates to a transport device which has a rotatable carrier on which the individual containers can also be held. The reference numeral 2 designates a housing, inside which the containers can be sterilised.

Figure 1B:
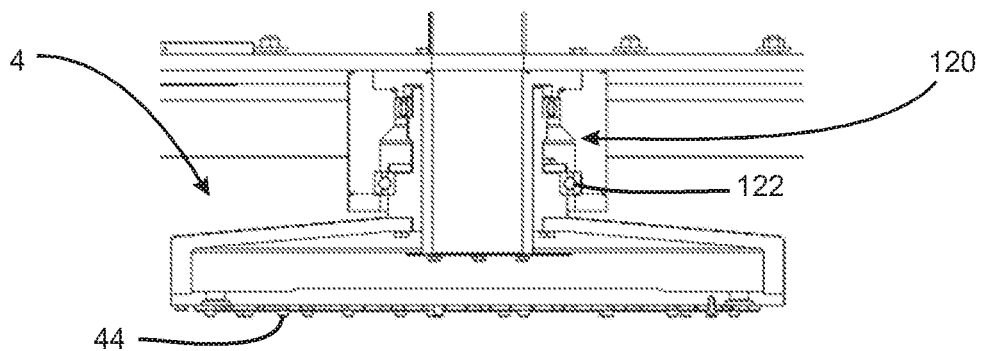

FIG. 1b shows a detailed representation of the machine shown in FIG. 1a. It will be recognised here that the distributor device 4 is supported by means of a rolling bearing 120 with bearing elements 122 on the cover of the machine. In this case this support is relatively complex.

Figure 1C:
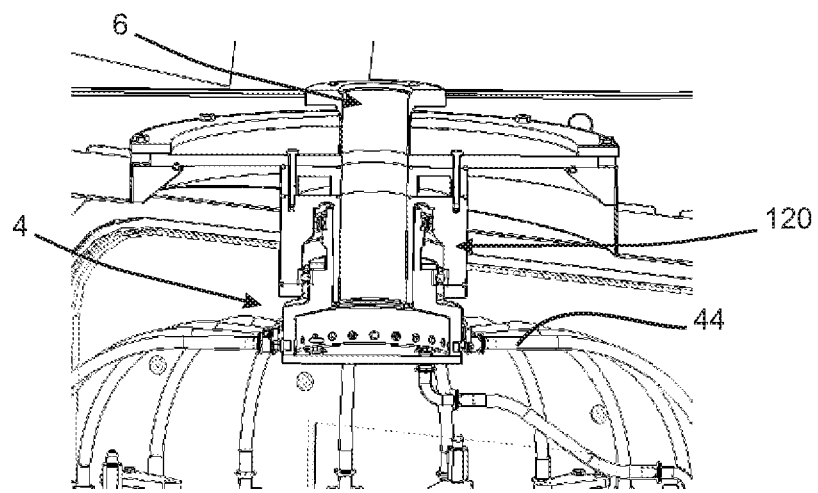

FIG. 1c shows a further representation of a machine according to the internal prior art of the applicant. It also shows the bearing device 120 which serves for supporting the distributor device 4. A feed conduit 6 is also provided, which is also arranged in a stationary manner here.

The reference numeral 44 relates to a conduit connection by means of which the flowable medium can ultimately be fed to the containers. The reference numeral 46 relates to an inlet conduit which forms a component of the inlet 42.

For sealing, in the embodiment shown in FIG. 1b both gap seals and also hybrid bearings or both can be used.

Figure 2:
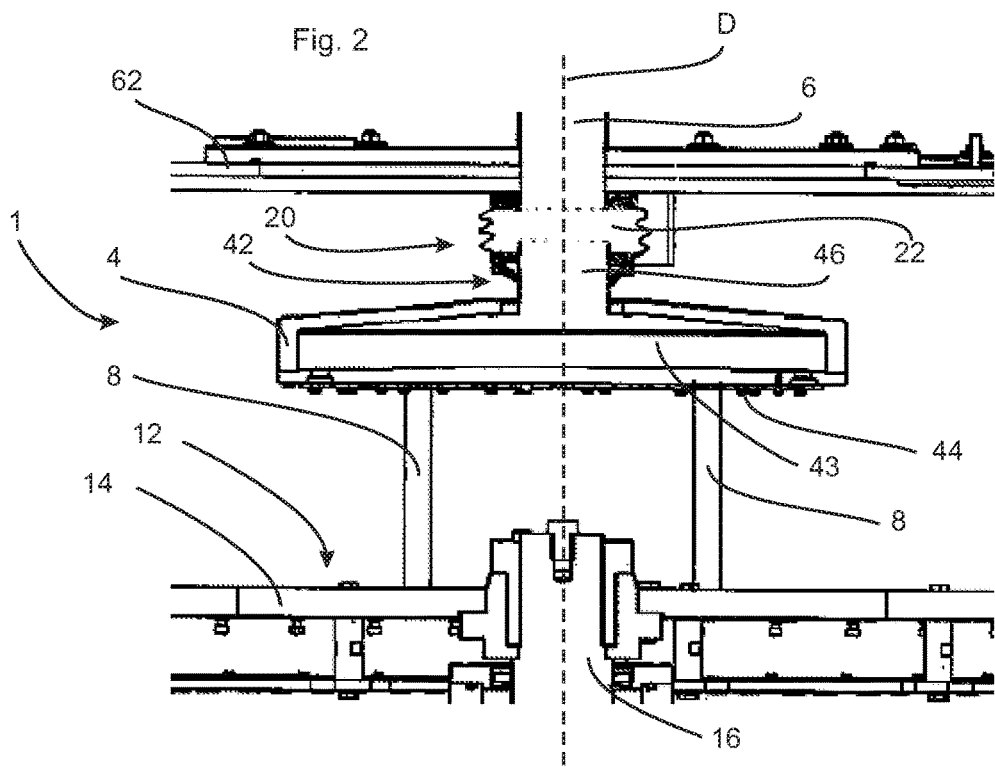
FIG. 2 shows a representation of a machine according to the invention.

FIG. 2 shows a schematic representation of a machine according to the invention. Here too the feed conduit 6 is again provided, which is arranged stationary on a cover 62 of the machine. The reference numeral 42 again designates the inlet, which rotates here with the distributor device 4.

The reference numeral 44 designates an outlet. Starting from the inlet 42, the flowable medium is distributed via a distribution compartment to this plurality of outlets 44. The reference numeral 43 designates a collecting compartment or a collecting chamber, which receives the flowable medium coming from the inlet 42 and distributes it to the individual outlets 44.

The reference numeral 12 again designates the transport device, and the reference numeral 14 designates the carrier on which the containers are held. The reference numeral 16 designates a drive shaft, by means of which the carrier 14 can be set in rotation.

Here the distributor device 4 is arranged by means of supporting rods 8 directly and also non-rotatably on the carrier 14. In this way the distributor device is also supported by this carrier 14. The $H_2O_2$ distributor chamber 4 is firmly connected in this way to the rotating processing wheel or transport wheel. As a result no more mounting is necessary. The connection between the stationary top and the rotating distributor chamber takes place by means of a bellows 22 with a shaft sealing ring. The bellows 22 is responsible for compensation for tolerances and the shaft sealing ring is responsible for the sealing. A co-rotation of the shaft sealing ring is avoided by means of a torque support.

Correspondingly the reference numeral 20 designates a connection point, in order to "mount" the inlet 42 rotatably relative to the feed conduit 6. More precisely, the reference numeral 22 here relates to a bellows which is a component of this sealing device. The reference numeral D designates an axis of rotation, with respect to which the distributor device 4 and also the carrier 14 are rotatable. However, instead of a bellows 22 with shaft sealing ring/sliding bearing bushing a lip seal application can be used.

Figure 3:
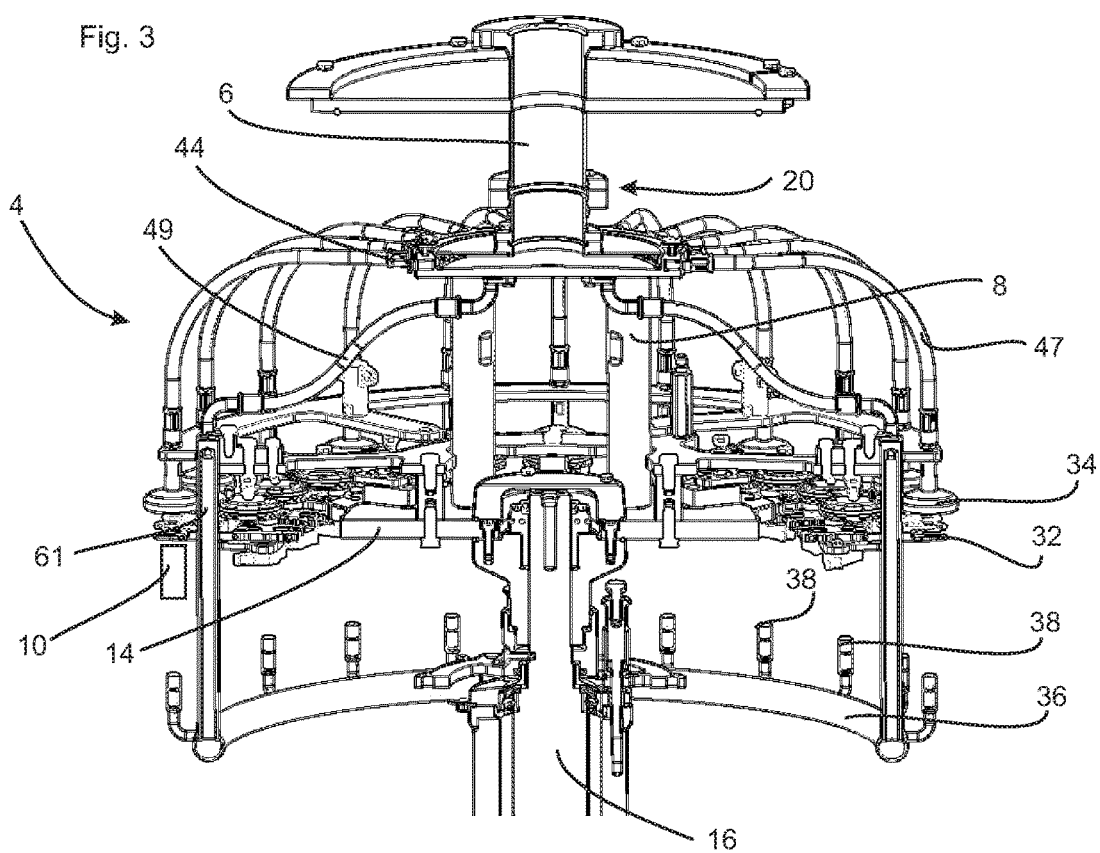
FIG. 3 shows a further more detailed representation of a machine according to the invention.

FIG. 3 shows a more detailed representation of a machine according to the invention. Here too the stationary feed conduit 6 and the supporting arrangement 20 are again provided. Here again the reference numeral 47 also designates feed conduits which convey the sterilising medium to the containers (not shown). The containers are preferably fastened to the carrier 14 here by means of retaining devices 32. The reference numerals 38 designate nozzles, by means of which a sterilising agent can be discharged and can sterilise the outer face of the preforms. The reference numeral 36 designates an annular channel which can be acted upon by the sterilising agent and/or which feeds and/carries the sterilising agent.

The reference numeral 34 designates further application devices, which acts upon at least the inner side of the containers with a sterilising agent. In this case such an application device 34 can advantageously be associated with each retaining device for a container. The reference numerals 49 designate further feed conduits, which convey the flowable medium to further application devices 36. The application devices 36 serve for the external sterilisation of the parisons and are supplied from the same $H_2O_2$ distributor chamber. Thus at least two feed conduits are preferably provided, which convey the flowable medium to different regions of containers. The reference numeral 61 designates further conduits which here convey the flowable medium in a vertical direction. In this case the distributor device 4 can have switching means (not shown), which enable selective supply of the feed conduits 49 or the feed conduits 47 with the flowable medium. However, these feed conduits 49 and 47 are preferably in use simultaneously and are preferably also supplied from the same distribution chamber.

Figure 4:
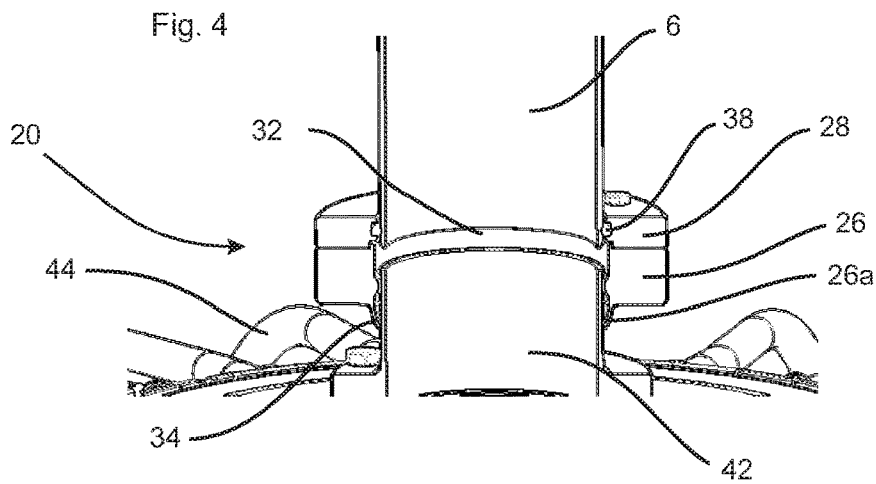
FIG. 4 shows a detailed representation of the machine shown in FIG. 3.

As shown in FIG. 4, in the embodiment shown in FIG. 3 a lip seal is used as the sealing device 20. In this case this lip seal has a fastening ring 28, on which the actual sealing means 26 is fastened. In this case this lip seal 26 has a sealing lip which preferably also allows a displacement of the components relative to one another (which can occur for example due to thermal expansion or concentricity errors). This sealing lip is designated by the reference numeral 26a. The main function of the sealing device is to seal off the transmission of the flowable medium. In addition, however, it is also conceivable that this sealing device also performs a certain interface function, in order to support the rotation of the inlet 42 relative to the feed device. However, the sealing device is preferably not capable of absorbing sufficient forces along the axis of rotation D, in order to hold only the distributor device 4.

Figure 5:
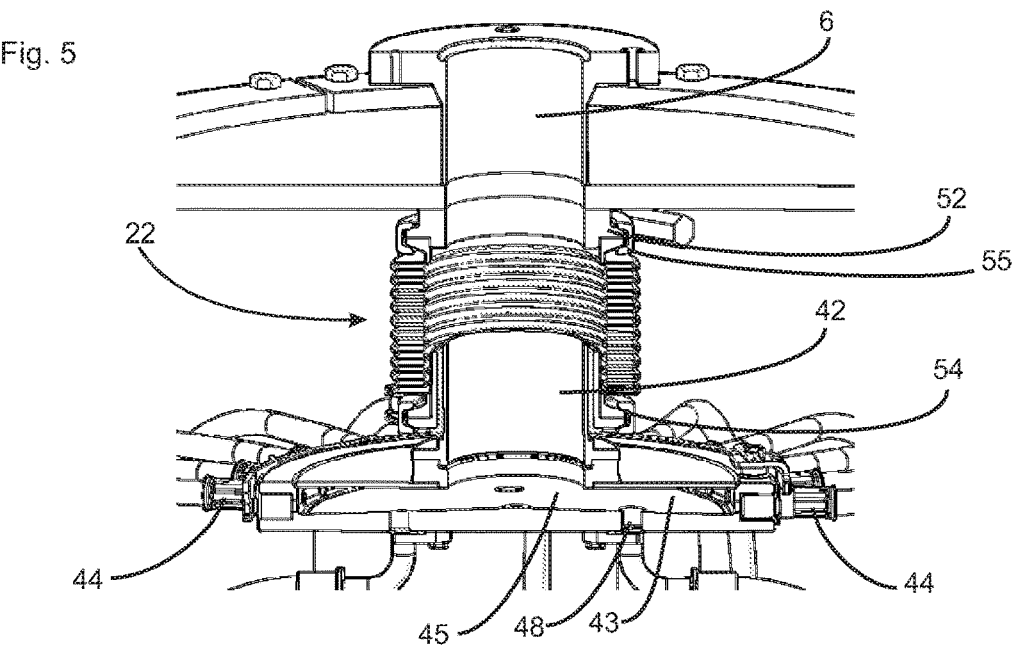
FIG. 5 shows a further embodiment of a machine according to the invention in which a bellows is used.
Figure 6:
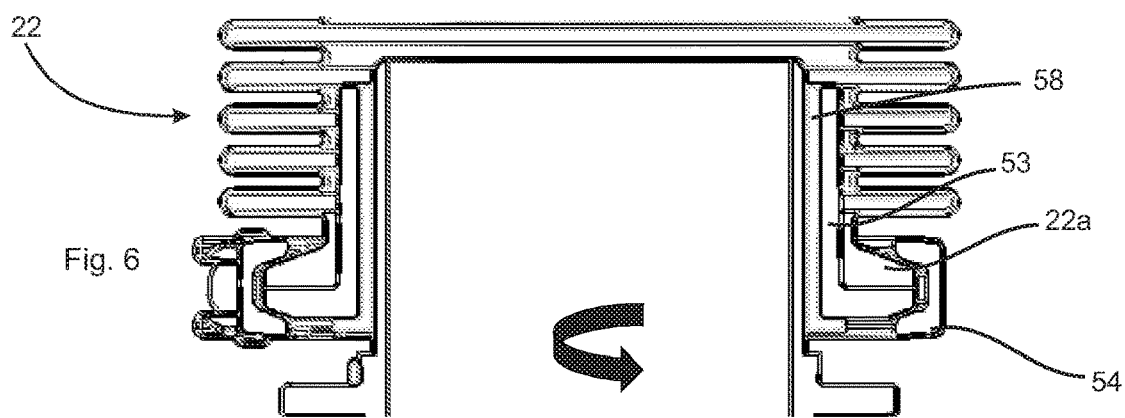
FIG. 6 shows a detailed representation shown in FIG. 5.

FIGS. 5 and 6 show a further embodiment of a machine according to the invention, wherein here the sealing device is configured as a bellows with a sliding bearing bushing. The bellows 22 here is suitable for compensating for a relative movement of the distributor device or the distributor disc 45 relative to the upper flange 52. Such relative movements can occur for example due to a thermal expansion of the housing. The reference numeral 54 relates to a clip which fastens a lower end 22a of the bellows 22 to a mounting 53. The reference numeral 58 designates a sliding bearing bushing, which is stationary here. Thus the entire sliding bearing functions as a gap seal and guides the bellows 22 in its lower region. The clips 54 and 55 (FIG. 5) preferably also serve here as quick-acting closures. In this way the entire sliding bearing bushing can be replaced in a short time. It has also been shown that a leakage loss is not greater than in the case of machines according to the internal prior art of the applicant. Openings 48 for discharging the flowable medium can also be provided in the above-mentioned distributor disc 45. Starting from these openings, the flowable medium enters the feed conduits 49 and thus the annular channel 36.

Figure 7:
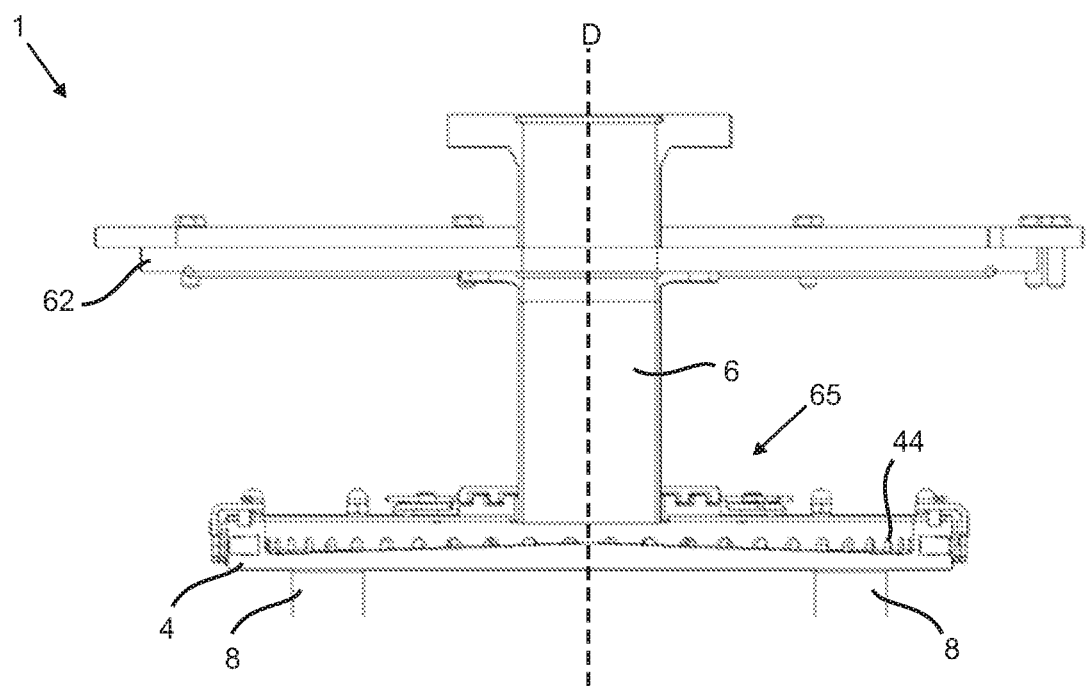
FIG. 7 shows a further embodiment of a machine according to the invention in which a labyrinth seal is used.
Figure 8:
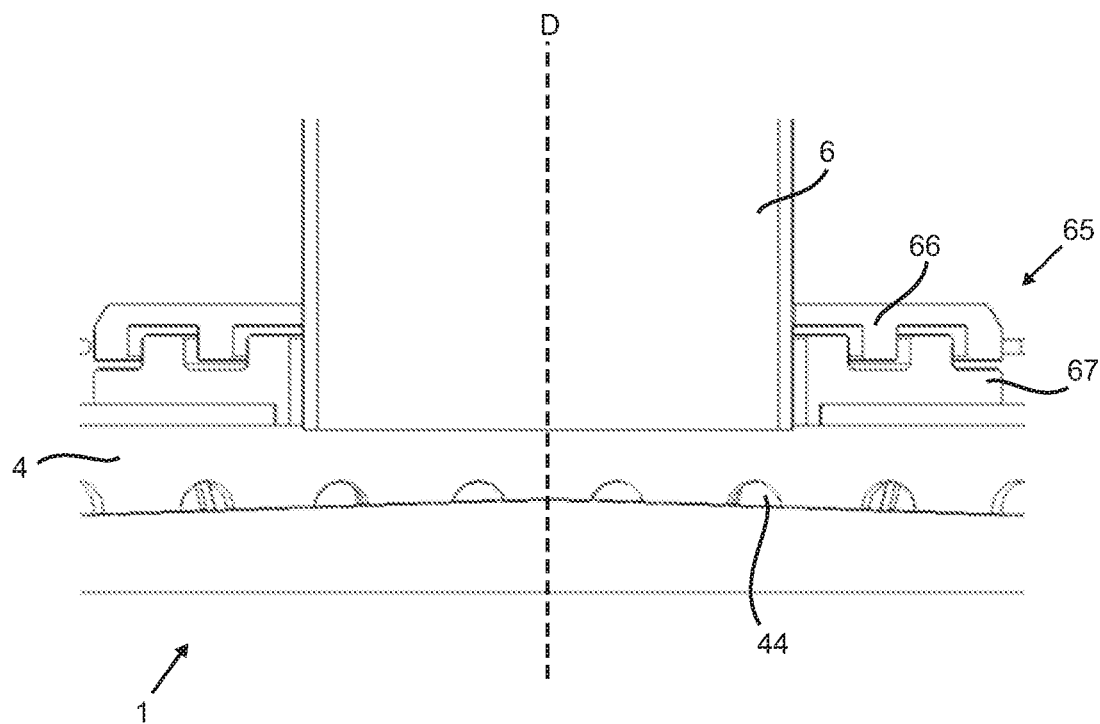
FIG. 8 shows a detailed representation shown in FIG. 7.

FIGS. 7 and 8 show a further embodiment of a machine according to the invention, wherein here a labyrinth seal 65 is provided as a seal between the feed conduit 6 and the distributor device 4. As can be seen in particular from FIG. 8, the labyrinth seal 65 is preferably constructed in two parts, wherein a first part 66 of the labyrinth seal is arranged on the stationary feed conduit 6 and a second part 67 of the labyrinth seal on the rotating distributor device 4. In this case the reference numeral 8 relates to supporting rods, so that also in this embodiment the distributor device 4 is arranged on the carrier. In this way, here too, the distributor chamber 4 is connected to the rotating processing wheel or transport wheel, so that there is no need for a mounting.

The applicant reserves the right to claim all the features disclosed in the application documents as essential to the invention in so far as they are individually or in combination novel over the prior art. Furthermore it is pointed out that features which may be advantageous per se have also been described in the individual drawings. The person skilled in the art recognises immediately that a specific feature described in a drawing may also be advantageous without the incorporation of further features from this drawing. Furthermore the person skilled in the art recognises that advantages may also result from a combination of several features shown in individual drawings or in different drawings.

LIST OF REFERENCES 1 machine
2 housing
4 distributor device
6 feed conduit
8 supporting rods
12 transport device with rotatable carrier
14 support
16 drive shaft
20 bearing device/sealing device
22 bellows
22a lower end of the bellows
26 sealing means
26a sealing lip
28 fastening ring
32 holding devices
34 further application devices
36 annular channel
38 nozzles
42 inlet
44 outlets
45 distributor disc
47 feed conduits
48 openings
49 feed conduits
52 upper flange
53 holder
54 clip 1
55 clip 2
58 sliding bearing bushing
61 conduits
65 labyrinth seal
66 first part of the labyrinth seal 65
67 second part of the labyrinth seal 65
120 rolling bearing, bearing device
122 bearing element
D axis of rotation

The invention claimed is:

1. A machine for distributing flowable media to containers, comprising:
   a housing, with a transport device for transporting the containers which is arranged at least partially inside the housing, wherein this transport device has a rotatable carrier;
   a distributor device which is arranged inside this housing which accommodates at least one inlet for the flowable medium and a plurality of outlets to which the flowable medium can be distributed; and
   a supply conduit which is suitable and intended for supplying the flowable medium to the inlet, wherein the distributor device is connected non-rotatably to the carrier, wherein a sealing device is arranged between the supply conduit and the distributor device, wherein the sealing device is suitable and intended for guiding the flowable medium from the supply conduit to the inlet, wherein the sealing device includes a contactless labyrinth seal, and wherein the supply conduit and the distributor device are constructed without contact, and wherein the sealing between the supply conduit and the distributor device takes place by the contactless labyrinth seal.

2. The machine according to claim 1, wherein the supply conduit is arranged, at least partially, non-rotatably with respect to the carrier and the distributor device is rotatable relative to the supply conduit.

3. The machine according to claim 1, wherein the transport device is a component of a processing device.

4. The machine according to claim 1, wherein the flowable medium is gaseous $H_2O_2$.

5. The machine according to claim 1, wherein at least the machine in its entirety is arranged in a clean room.

6. The machine according to claim 1, wherein the inlet comprises an inlet conduit which is arranged non-rotatably on the distributor device and is fluidically connected to the supply conduit.

7. The machine according to claim 6, wherein the sealing device is arranged between the inlet conduit and the supply-conduit.

8. The machine according to claim 7, wherein the sealing device is configured as a shaft sealing ring.

9. The machine according to claim 1, wherein the sealing device comprises a resilient element along the axis of rotation.

10. The machine according to claim 9, wherein the resilient element connects the supply conduit to the inlet of the distributor device.

11. A method for processing containers, wherein the containers are transported by means of a transport device and being acted upon during this transport by a flowable medium, and wherein the transport device has a rotatable carrier, by means of which the containers are transported along a substantially circular path and this carrier is located inside a housing, wherein the flowable medium is fed by means of a supply conduit to a distributor device likewise located inside this housing via an inlet and the distributor device distributes the flowable medium to a plurality of outlets, wherein the distributor device is non-rotatably connected to the rotatable carrier, wherein a sealing device is arranged between the supply conduit and the distributor device, wherein the sealing device is suitable and intended for guiding the flowable medium from the supply conduit to the inlet, wherein the sealing device includes a contactless labyrinth seal, and wherein the supply conduit and the distributor device are constructed without contact, and wherein the sealing between the supply conduit and the distributor device takes place by the contactless labyrinth seal.

* * * * *